US00PP19927P3

(12) United States Plant Patent
Hummel

(10) Patent No.: US PP19,927 P3
(45) Date of Patent: Apr. 14, 2009

(54) ***CORDYLINE* PLANT NAMED 'SEIPIN'**

(50) Latin Name: *Cordyline australis*
Varietal Denomination: Seipin

(76) Inventor: Paul A. H. Hummel, Seiont Nurseries, Caer Glyddyn Rhosbodrual, Caernarfon, Gwynedd (GB), LL55 2BB ( * ) Notice: Subject to any disclaimer, the term of this patent is extended or adjusted under 35 U.S.C. 154(b) by 0 days.

(21) Appl. No.: 11/998,259

(22) Filed: Nov. 29, 2007

(65) Prior Publication Data

US 2008/0184430 P1 Jul. 31, 2008

Related U.S. Application Data

(60) Provisional application No. 60/880,666, filed on Jan. 16, 2007.

(51) Int. Cl.
*A01H 5/00* (2006.01)

(52) U.S. Cl. ..... Plt./383

(58) Field of Classification Search ..... Plt./383
See application file for complete search history.

*Primary Examiner*—Annette H Para
*Assistant Examiner*—Georgia Helmer
(74) *Attorney, Agent, or Firm*—Penny J. Aguirre

(57) ABSTRACT

A new cultivar of *Cordyline australis,* 'Seipin', characterized by its foliage that exhibits greyed purple centers and bright pink margins.

2 Drawing Sheets

Botanical classification: *Cordyline australis.*
Cultivar designation: 'Seipin'.

BACKGROUND OF THE INVENTION

The present invention relates to a new and distinct cultivar of *Cordyline australis* and will be referred to hereafter by its cultivar name, 'Seipin'. 'Seipin' represents a new cultivar of cabbage tree or cabbage palm and is grown as a foliage plant for landscape and container use.

The inventor discovered and the new cultivar as a naturally-occurring chimeral mutation of *Cordyline australis* 'Red Star' (not patented) in a tissue culture lab in Lancashire, United Kingdom in 2002.

Asexual reproduction of the new cultivar was first accomplished by in vitro leaf base propagation in 2002 in Lancashire, United Kingdom under the direction of the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Seipin' as a new and unique cultivar of *Cordyline.*

1. 'Seipin' exhibits foliage that is greyed purple in color with pink variegation on the margins of the leaves.
2. 'Seipin' is readily propagated by tissue culture.

In comparison to the parent plant, 'Red Star', 'Seipin' has greyed purple foliage with bright pink margins on its leaves whereas 'Red Star' lacks the pink margin on its leaves.

In comparison to the *Cordyline australis* cultivar 'Pink Stripe' (not patented), 'Seipin' has pink variegation on the margins of its leaves whereas 'Pink Stripe' has pink variegation in the center of its leaves. In comparison to the

*Cordyline australis* cultivar 'Pacific Coral' (not patented), 'Seipin' has greyed purple leaves with pink margins whereas 'Pacific Coral' has olive green leaves with Pink margins.

BRIEF DESCRIPTION OF THE DRAWING

The accompanying colored photographs illustrate the overall appearance and distinct characteristics of the new *Cordyline.* The photographs in FIG. 1 and FIG. 2 were taken of a 2 year-old plant of 'Seipin' as grown outdoors in a 22 cm container in Lancashire, United Kingdom.

Figure 1:
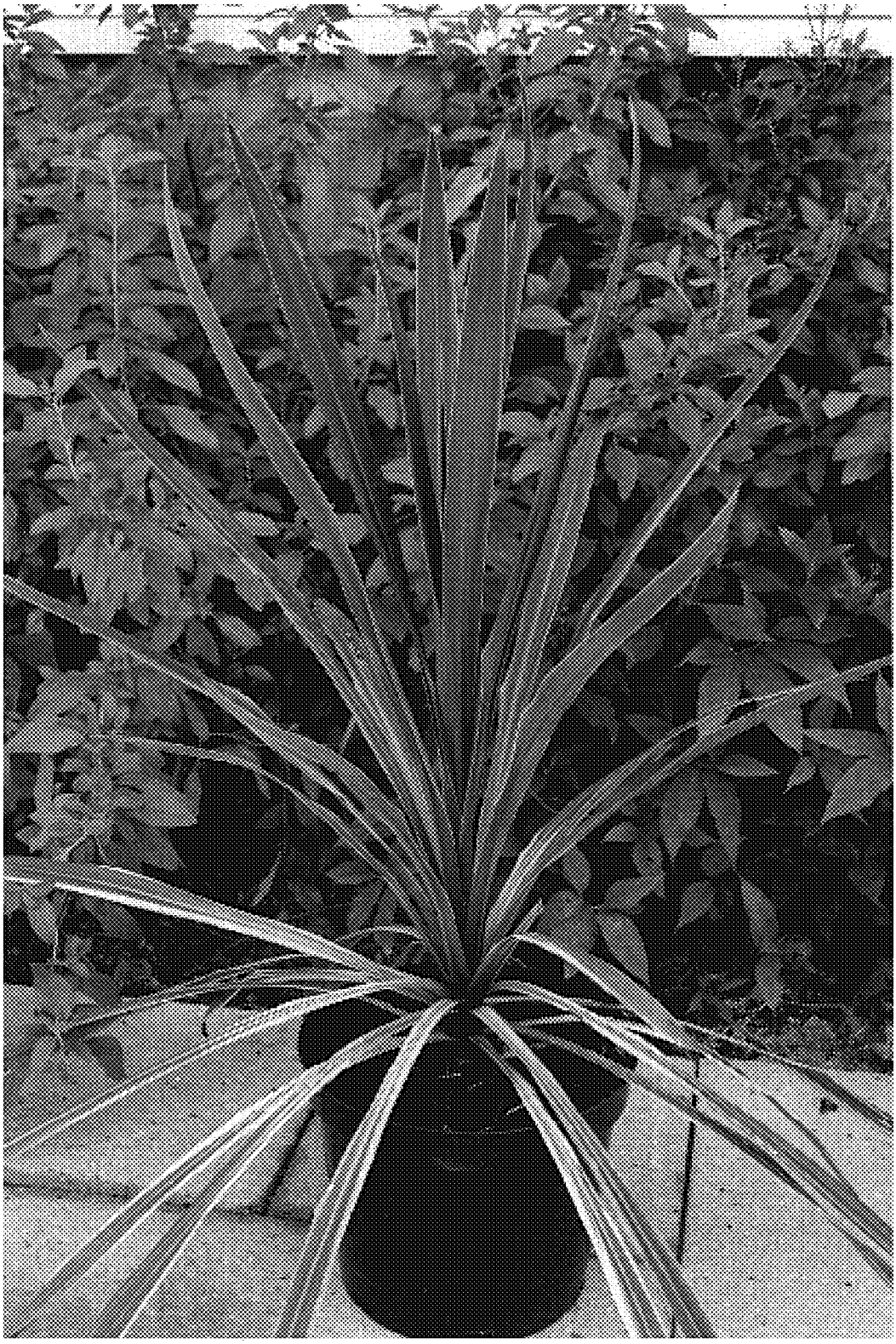
FIG. 1 provides a side view of 'Seipin' and FIG. 2 provides a close up view of the stem of 'Seipin'.
Figure 2:
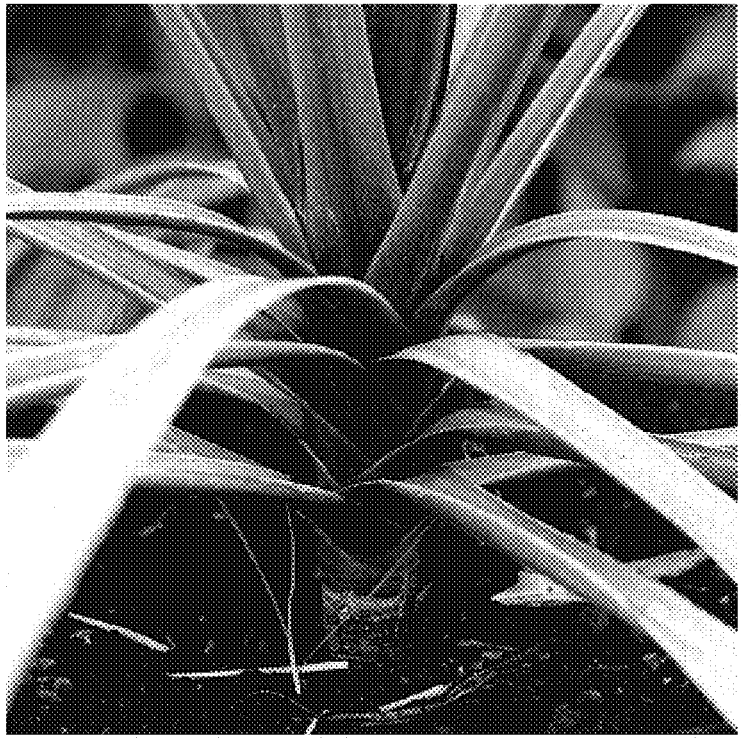
Figure 3:
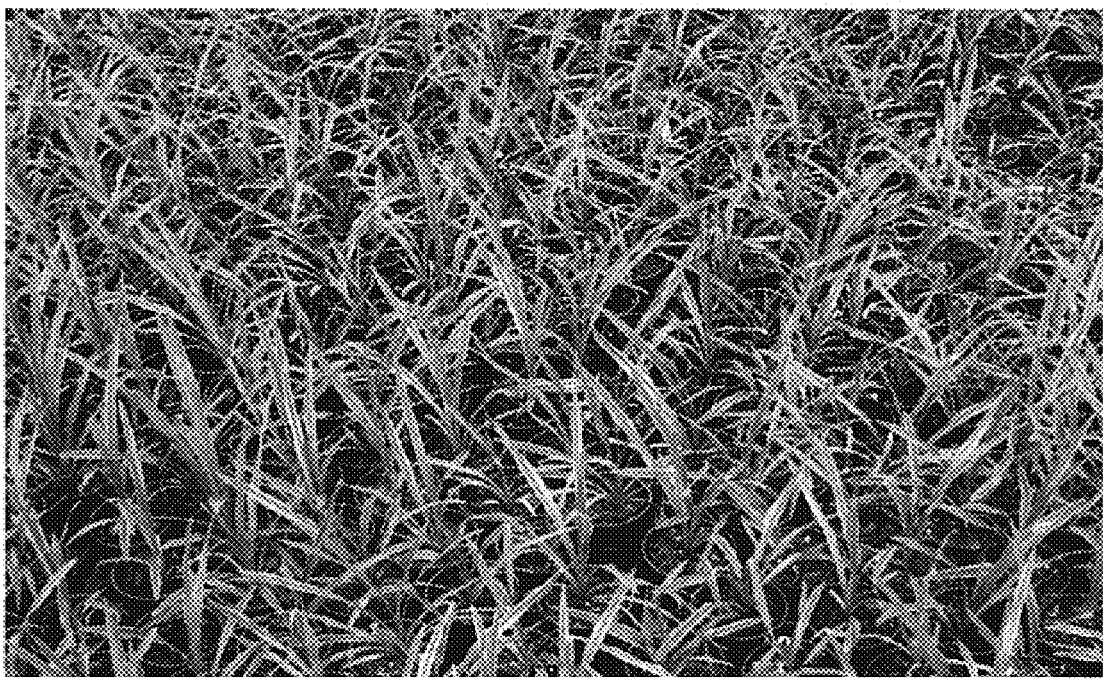
FIG. 3 was taken of 3 month-old plants and illustrates the uniformity of 'Seipin'.

The colors in the photographs are as close as possible with the photographic and printing technology utilized. The color values cited in the detailed botanical description accurately describe the colors of the new *Cordyline.*

DETAILED BOTANICAL DESCRIPTION OF THE PLANT

The following is a detailed description of 2 year-old plants of the new cultivar as grown outdoors in Lancashire, United Kingdom. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

Botanical classification: 'Seipin' is a cultivar of *Cordyline australis.*

Parentage: Naturally-occurring chimeral mutation of *Cordyline australis* 'Red Star'.

Blooming period.— No flower production has been observed for 'Seipin'.

General Description:

*Plant habit.*—Evergreen tropical perennial, upright, solitary stem.

*Height and spread.*—Reaches about 60 cm in height and 50 cm in width.

*Hardiness.*—U.S.D.A. Zone 10.

*Culture.*—Well drained soils in full sun in the United Kingdom.

*Diseases and pests.*—No unique susceptibility or resistance to diseases or pests has been observed.

*Root description.*—Fibrous.

*Propagation.*—Tissue culture.

*Growth rate.*—Moderate, vigor typical to other cultivars of *Cordyline australis*.

Stem description:

*Stem length.*—1 to 2 cm to lowest leaves.

*Stem width.*—Average of 1.6 cm.

*Stem cross-section.*—Round, solid.

*Stem surface.*—Cork-like.

*Stem color.*—Primarily 199D.

Foliage description:

*Leaf shape.*—Linear.

*Leaf division.*—Simple.

*Leaf base.*—Narrowing into an indistinctly defined sheathed petiole.

*Leaf apex.*—Acuminate.

*Leaf venation.*—Longitudinal, parallel, not prominent, same color as leaves.

*Leaf margins.*—Entire, weakly revolute.

*Leaf attachment.*—Sheathed with ill defined petiole.

*Leaf arrangement.*—Whorled in tight rosette.

*Leaf orientation.*—Held upright and up to a 45° angle.

*Leaf substance.*—Thick, leathery.

*Leaf surface.*—Glabrous, dull, weakly carinate.

*Leaf color.*—Young and mature leaves upper surface; closest to N186A with a marginal band and a few streaks of 59C, the marginal band and streaks become broader towards base, young and mature leaves lower surface; color between N187A and N187B with a marginal band and a few streaks of 186A, the marginal band and streaks become broader towards base.

*Venation.*—Parallel, mid rib 185D on upper surface and same color as leaf on lower surface.

*Leaf size.*—Average of 54 cm in length and 3 cm in width.

*Petiole.*—Weakly defined about 10 cm in length and 2 cm in width, color of upper surface is 59A with a faint greyer central stripe and 157A near attachment, color of lower surface is 186A with a center band that is greyer in color (no color code match).

I claim:

1. A new and distinct cultivar of *Cordyline* plant named 'Seipin' as herein illustrated and described.

* * * * *